United States Patent [19]

Link et al.

[11] Patent Number: 4,698,063
[45] Date of Patent: Oct. 6, 1987

[54] DEVICE FOR EMBEDDING IN BONE, IN PARTICULAR A FEMORAL HIP-JOINT PROSTHESIS

[76] Inventors: Helmut D. Link, Wildstieg 14, 2000 Hamburg 65; Arnold Keller, An der Naherfurth 5, 2061 Kayhude, both of Fed. Rep. of Germany

[21] Appl. No.: 795,368

[22] Filed: Nov. 6, 1985

Related U.S. Application Data

[63] Continuation of Ser. No. 472,853, Mar. 7, 1983, abandoned.

[30] Foreign Application Priority Data

May 3, 1982 [DE] Fed. Rep. of Germany ....... 3216538

[51] Int. Cl.$^4$ .............................................. A61F 2/32
[52] U.S. Cl. ......................................... 623/23; 623/16
[58] Field of Search ........................ 623/16, 17, 18, 19, 623/20, 21, 22, 23; 128/92 YP, 92 YF

[56] References Cited

FOREIGN PATENT DOCUMENTS 1099519 9/1955 France ................................. 623/23

*Primary Examiner*—Richard J. Apley
*Assistant Examiner*—David Isabella
*Attorney, Agent, or Firm*—Chilton, Alix & Van Kirk

[57] ABSTRACT

A device for embedding in bone, in particular as a femoral hip-joint prosthesis, comprises a head part, a stem to be anchored in the bone, and a support collar terminating the stem at the head end. In order to make it easy for the surgeon, on reoperation, to remove the prosthesis stem from the bone tissue, the support collar can be removed. In addition, it can be combined with an anchor for attachment to the greater trochanter. By this means, on the one hand, the support collar is fixed in the envisaged position and, on the other hand, the greater trochanter participates with the adjacent lateral areas of the bone in taking up the load.

15 Claims, 6 Drawing Figures

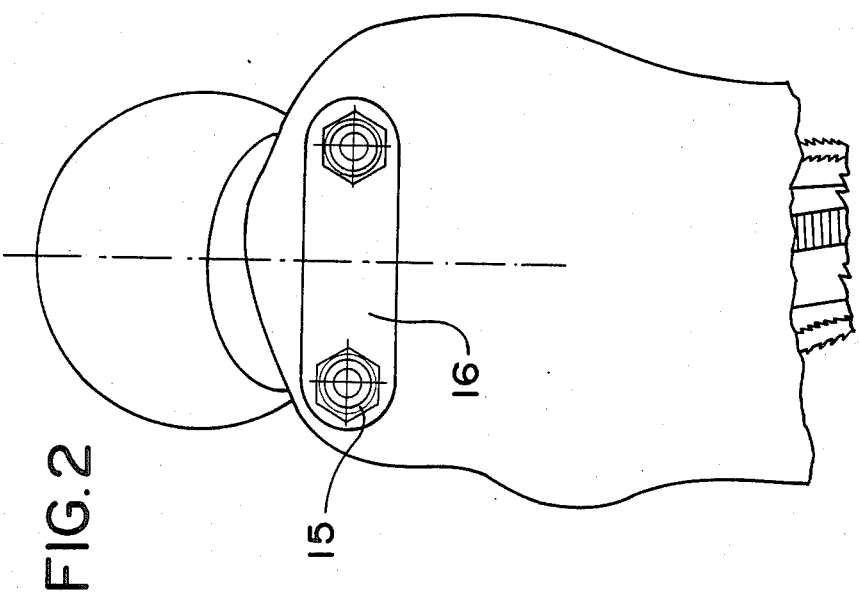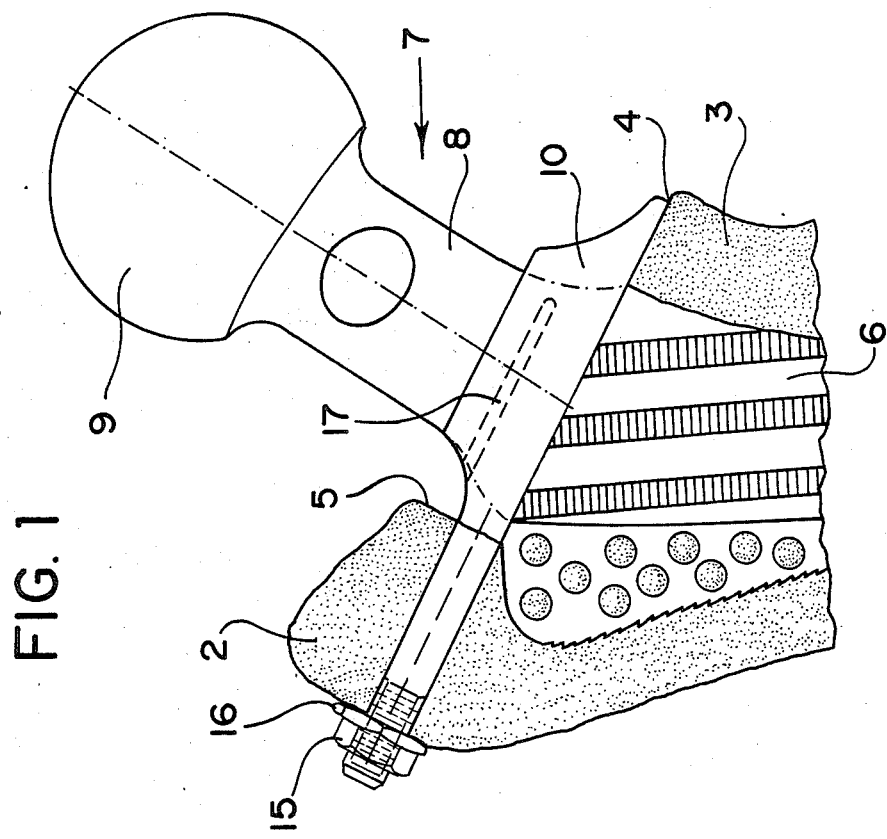

DEVICE FOR EMBEDDING IN BONE, IN PARTICULAR A FEMORAL HIP-JOINT PROSTHESIS

This application is a continuing application of U.S. Ser. No. 472,853 filed Mar. 7, 1983, abandoned.

DESCRIPTION

The invention relates to a device for embedding in bone, in particular a femoral hip-joint prosthesis, having a head part, a stem to be anchored in the bone and a support neck terminating the stem at the head end.

When the prosthesis needs to be removed during the course of reoperation, it is frequently necessary to break the bond between the prosthesis stem and the bone tissue or the bone cement using a bone chisel. However, this can meet difficulties when the prosthesis stem is terminated at the head end by a so-called support neck or collar. This is generally an encircling projection in the shape of a plate or collar which is supported on the proximal surface of resection of the bone. For this reason, some surgeons have changed over to using prostheses not having support collars, although the combined action of the support collar with the surface of resection is without doubt, as a consequence of its favourable position in relationship to the direction of force, able to make a valuable contribution to the overall transmission of load.

Thus, the invention is based on the object of producing a device for embedding in bone of the type mentioned in the introduction which can be removed more easily without it being necessary for this reason to dispense with the support collar.

This is achieved, according to the invention, by it being possible for the support collar to be put in place and removed when the prosthesis is in place.

If the prosthesis has to be removed, initially the support collar is removed. By this means, the surgeon achieves ready access to the stem and can break the bond between prosthesis and bone using the bone chisel.

Since the head of the femur is displaced laterally with respect to the axis of the thigh bone, when standing, the thigh bone is subjected to a bending stress which brings about tensile stress laterally and compressive stress medially in the bone. When the head and neck of the thigh bone are replaced by a stem prosthesis, the stem of which is anchored in the medullary cavity of the bone, then the line of force in the bone changes fundamentally. In particular, the lateral side is completely relieved of tensile forces, while large compressive forces need to be transmitted medially from the prosthesis stem to the bone tissue. Both the lateral relief of the bone and any other loading in the medial region can lead to manifestations of degeneration and subsequent loosening of the prosthesis.

The invention has recognized that the lateral region of the bone, in particular including the bone at the prosthesis end, can participate in transmitting the force by the support collar surrounding the prosthesis having, on the side facing away from the greater trochanter, an anchor for attachment to the greater trochanter. The support collar fixed to the greater trochanter thus becomes an element which supports the prosthesis against those forces which are trying to force it medially. On the one hand, by this means the medial side of the bone is relieved while, on the other hand, the relieving forces must be taken up by the greater trochanter and thus by the lateral side of the bone adjacent thereto.

The anchoring of the support collar to the greater trochanter can assume any suitable form. It is particularly advantageous to construct the support collar in the shape of a hook or horseshoe and to have the anchor engage the free end of the hook or the ends of the horseshoe.

In some cases, it is unnecessary to fix the support collar with respect to the longitudinal axis of the prosthesis. Even when fixing is omitted, the support collar supports the prosthesis not only against forces acting medially but it also transmits a part of the vertical forces to the surface of resection of the bone. However, it is usually advantageous to provide the support collar, and the seating provided for it on the prosthesis, with ribs and grooves which run at right angles to the axis of the stem or neck and act together. After insertion of the prosthesis into the bone tube, the support collar is fixed to the prosthesis by advancing it, at right angles to the axis of the prosthesis and coinciding with the axis of the ribs and grooves, onto the prosthesis so that it grips it on both sides. The gripping action of the collar on the prosthesis prevents longitudinal movement of the collar on the neck with the frictional engagement of the collar and neck, especially at the ribs and grooves, tending to retain the collar against lateral movement. It is then anchored to the greater trochanter.

The invention is illustrated in more detail below with reference to the drawing which depicts an advantageous exemplary embodiment. In this:

FIG. 1 shows a lateral-medial section through the upper end of a thigh-bone provided with a stem prosthesis, FIG. 2 shows a lateral view of the same parts.

Figure 5:
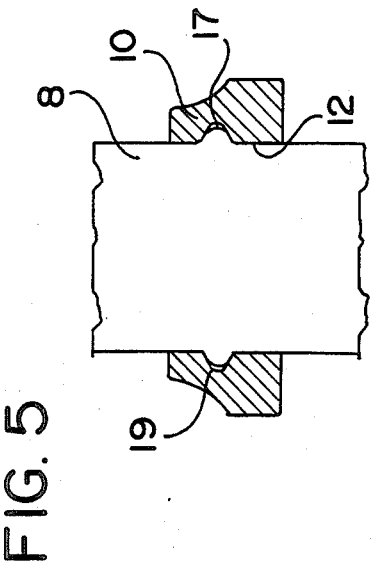
FIG. 5 is a longitudinal sectional view, partly broken away, of the collar mounted to the neck of the prosthesis.

In the view of the section, the thigh-bone 1 is indicated by a dotted line and its greater trochanter is indicated by 2, while the medially opposing regions of bone are designated with 3. The neck of the femur is separated from the head of the femur along the surface of resection 4 and 5.

The stem 6 of the prosthesis 7, which carries the head 9 on the neck 8, is inserted into the medullary cavity. The support collar 10, which is located with its undersurface 11, at least medially but also ventrally and dorsally to a certain extent, on the surface of resection 4 is located at the transition from the neck 8 to the stem 6. Its internal surfaces 12 are suited to the external shape of the seating of the prosthesis which receives it. The support collar is constructed in the shape of a horseshoe, two bolts 13 being attached to the ends of the horseshoe, which bolts pass through drillings in the greater trochanter and have, on the end, a screw thread 14 which makes it possible to anchor with nuts 15 via a pressure plate 16. The anchoring is adjusted such that both the greater trochanter 2, via the anchoring 15, 16, and also the medial area of the bone 3, via direct contact with the adjacent part of the stem 6, participate in the bone taking up the forces acting medially on the prosthesis.

The seating surface 12 of the support collar is provided with grooves 17 and the associated seating surface of the prosthesis is provided with corresponding ribs 19 to be received in the grooves to fix the collar to the stem. The ribs and grooves act together and run approximately in the direction of the bolts 13 at right angles to the axis of the stem or neck so that they engage together, by advancing laterally the support collar on the associated seating of the prosthesis, and they are able to transmit the forces arising in the longitudinal axis of the prosthesis. The prosthesis and support collar are configured so that the support collar is fixed to the prosthesis by advancing the collar onto the prosthesis at a right angle to the axis of the prosthesis coinciding with the axis of the ribs and grooves so that the collar grips the prosthesis on both sides. The gripping action of the collar on the prosthesis prevents longitudinal movement of the collar on the neck with the frictional engagement of the collar and neck, especially at the ribs and grooves, tending to retain the collar against lateral movement. In some applications, this lateral retention of the collar on the prosthesis is sufficient so that securement to the trochanter is not required. Where additional lateral securement is desired, the collar may be fixed to the trochanter or, alternately, the collar may be provided with additional means for fixing it to the prosthesis such as a retainer screw or a wire binding the collar and prosthesis.

Figure 6:
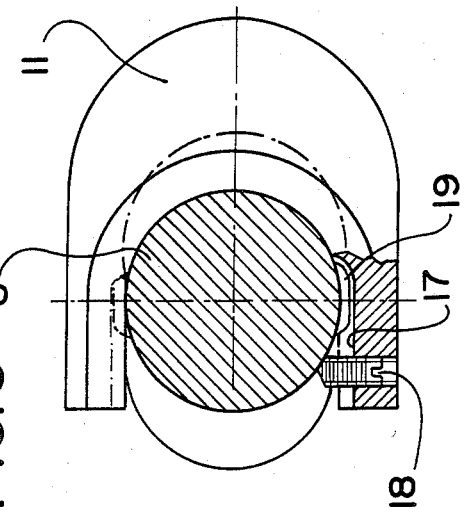
FIG. 6 is a sectional view of a further embodiment of the present invention.
Figure 3:
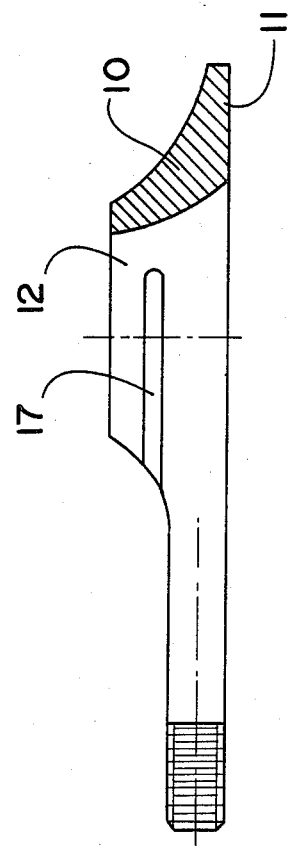
FIG. 3 shows a longitudinal section through the support collar.
Figure 4:
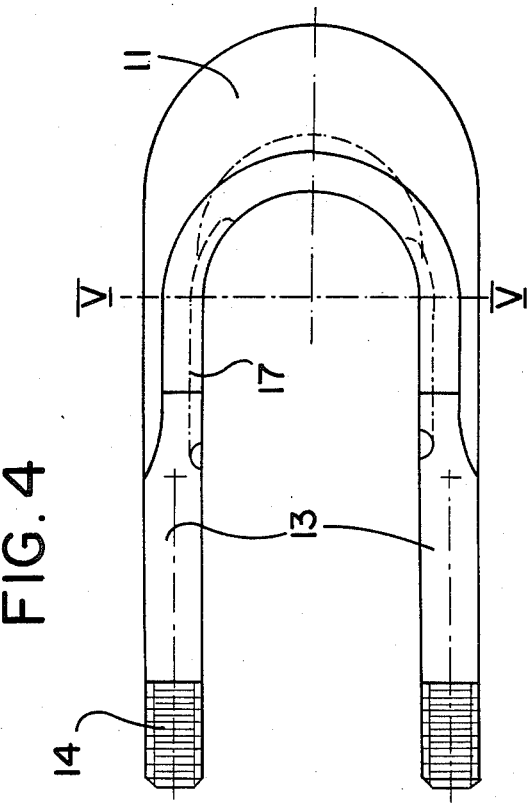
FIG. 4 shows a top view of the support collar.

Referring to FIG. 6, an embodiment of the present invention is shown wherein the support collar is not secured to the trochanter and a retainer screw 18 is utilized to laterally secure the support collar 12' on the neck 8. The retainer screw 18 is threadably mounted in one side of the support collar so as to allow the screw 18 to engage the side of the neck 8 adjacent the trochanter to laterally lock the collar on the neck. In operation, the screw 18 is in a retracted position while the collar is slidably mounted on the neck in the manner previously described with respect to the embodiments of FIGS. 1–5. After mounting, the screw 18 is rotated so as to project inwardly from the side of the support collar into engagement with the neck 8 to laterally retain the collar on the neck 8. The collar 12' is not directly secured to the trochanter and to remove the collar 12', the screw 18 is rotated so as to withdraw the screw within the support collar out of engagement with the neck before the support collar is slidably withdrawn from the neck. As in the embodiment of FIGS. 1–5, the collar provides an opening in the form of an open-ended recess to permit removal of the collar from the neck while the stem portion remains anchored in the femur bone. Other acceptable means may be utilized for providing an opening of sufficient size to allow selective removal of the collar from the neck such as a disassemblable collar which partially disassembles to provide an opening for withdrawal of the collar from the neck.

In each embodiment, the support collar is removeable while the stem remains anchored in the femur bone. In the case of reoperation, the support neck can be removed before the surgeon starts to break the bond between the bone and prosthesis stem.

The prosthesis is also suitable for use in those cases where it is intended entirely to dispense with a support collar for reasons other than those described.

We claim:

1. A hip-joint prosthesis comprising:
   a head portion,
   a stem portion adapted to be anchored in a femur bone,
   a neck portion interconnecting said head and said stem portions, and
   a removable support collar for mounting to said neck portion in a fixed position in engagement with the end of a femur bone, said collar being U-shaped and having a first open end and an opposing enclosed end and
   having first and second sides defining a recess portion configured to receive said neck portion when said collar is mounted to said neck portion, said neck portion and said recess portion having cooperating means for selectively mounting said support collar in a fixed position on said stem and removing said support collar from said neck portion while said stem portion is anchored in a femur bone, said first end forming an opening of sufficient size for passage of said neck portion therethrough to permit selective removal of said collar from said neck portion while said stem portion is anchored in a femur bone, and
   a bottom surface adapted to rest upon the end of the femur bone so as not to extend into the femur bone to facilitate removal of said collar from said neck portion while said stem portion is anchored in a femur bone.

2. The device of claim 1 wherein said neck portion has a neck seat portion to engage said collar and said collar has a corresponding collar seat portion to engage said neck seat portion when said collar is mounted about said stem portion, one of said neck seat portion and said collar seat portion having ribs and the other of said neck seat portion and said collar seat portion having corresponding grooves to receive said ribs to fix said collar to said neck portion.

3. The device of claim 2 wherein said ribs and grooves are disposed orthogonally to the longitudinal axis of said neck portion when said collar is mounted to said neck portion.

4. The device of claim 1 which comprises means for detachably securing said collar to the greater trochanter to permit securement of said collar to the greater trochanter when said collar is mounted about said neck portion and detachment of said collar from the greater trochanter when said collar is removed from said neck portion while said stem portion remains anchored in the femur bone.

5. The device of claim 4 wherein said collar has first and second distal ends for securement to the greater trochanter.

6. The device of claim 5 wherein said neck portion has first and second sides with said first side adapted to face the greater trochanter and said second side adapted to face away from the greater trochanter, said collar encompassing the second side of said neck portion.

7. In combination,
   a femur bone including a greater trochanter and a medullary cavity and having a resection surface adjacent the greater trochanter, and
   a hip-joint prosthesis comprising,
   a stem portion anchored within the medullary cavity of the femur bone,
   a head portion,
   a neck portion interconnecting said stem portion and said head portion, said stem portion and said head portion being exterior to said medullary cavity, a removable support collar having
   first and second opposing sides defining a recess portion configured to receive said neck portion when said collar is mounted to said neck portion, said recess portion and said neck portion having cooperating means for alternately selectively detachably mounting said support collar in a fixed position to said neck portion and removing said collar from said neck portion while said stem portion is anchored in a femur bone,
   a bottom surface adapted to rest upon said resection surface of the femur bone so as not to extend into the femur bone to facilitate removal of said collar from said neck portion while said stem portion is anchored in a femur bone, and
   means for providing an opening for said neck portion in said collar of sufficient size to permit passage of said neck portion therethrough for selective removal of said collar from said neck portion while said stem portion is anchored in the femur bone,
   said collar being detachably mounted to said neck portion in a fixed position with said bottom surface abutting said resection surface so as not to extend into said medullary cavity whereby said collar is removable from said neck portion while said stem portion remains anchored within said medullary cavity,
   said neck portion having a neck seat portion to engage said collar and said collar having a corresponding collar seat portion to engage said neck seat portion when said collar is is mounted about said neck portion, one of said neck seat portion and said collar seat portion having ribs and the other of said neck seat portion and said collar seat portion having corresponding grooves to receive said ribs to fix said collar to said neck portion.

8. The combination of claim 7 which comprises means for detachably securing said collar to said greater trochanter and said collar is detachably secured to said greater trochanter.

9. The combination of claim 8 wherein said collar has first and second distal ends secured to the greater trochanter and a recessed central portion about said neck portion.

10. The combination of claim 9 wherein said greater trochanter has two apertures to receive said first and second distal ends respectively and said securement means comprises threaded fastener means to secure said distal ends to said greater trochanter.

11. The combination of claim 10 wherein said distal ends are threaded and corresponding threaded fasteners engage said threaded ends to detachably secure said collar to said greater trochanter.

12. The combination of claim 1 wherein said ribs and grooves are disposed orthogonally to the longitudinal axis of said neck portion when said collar is mounted to said neck portion.

13. The combination of claim 7 wherein said support surface of said collar is planar to permit slidable removal of said collar over said resection surface.

14. A method of removing a prosthesis from a femur bone wherein the prosthesis includes a support collar supported upon the resection surface of the femur bone along a generally laterally extending interface comprising the steps of removing the support collar from the prosthesis by slidably withdrawing the collar laterally from the neck prior to removing the prosthesis from the femur bone.

15. The method of claim 14 wherein the prosthesis comprises a neck which is received by the collar and further comprising removing the support collar by withdrawing the support collar from the prosthesis so that the neck of the prosthesis passes through an opening in the collar.

* * * * *